United States Patent [19]

Costanzo et al.

[11] Patent Number: 5,384,327
[45] Date of Patent: Jan. 24, 1995

[54] ANTICONVULSANT SORBOPYRANOSE SULFAMATES

[75] Inventors: Michael J. Costanzo, Ivyland; Bruce E. Maryanoff, New Hope, both of Pa.

[73] Assignee: McNeilab, Inc., Spring House, Pa.

[21] Appl. No.: 994,735

[22] Filed: Dec. 22, 1992

[51] Int. Cl.$^6$ ............... A61K 31/35; C07D 311/94
[52] U.S. Cl. ........................ 514/456; 549/396
[58] Field of Search ................... 549/396; 514/456

[56] References Cited

PUBLICATIONS

Maryanoff et al., J. Med. Chem., 30(5), 880–7 (1987).

Primary Examiner—Nicky Chan
Attorney, Agent, or Firm—Ralph R. Palo

[57] ABSTRACT

Sulfamate derivatives having the following formula (I):

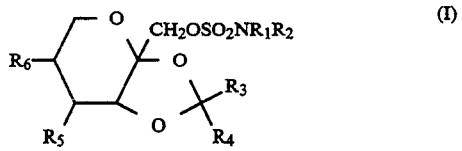

wherein $R_1$, $R_2$, $R_3$, $R_4$, $R_5$, and $R_6$ are as herein defined, have been found to exhibit anticonvulsant activity and are thus useful in the treatment of conditions such as epilepsy. Further, the present invention encompasses pharmaceutical compositions containing a compound of formula (I) as well as methods for their use and novel intermediates are disclosed.

9 Claims, No Drawings

ANTICONVULSANT SORBOPYRANOSE SULFAMATES

BACKGROUND OF THE INVENTION

Sulfamates of various structures, including those derived from monosaccharides, are described in J. Med. Chem. 1987, 30, 880 and in U.S. Pat. No. 4,075,351. Certain of these sulfamates are useful as pharmaceutical agents. More recently, sulfamates having various pharmaceutical activity in the areas of epilepsy, glaucoma, peptic ulcers, and male infertility are described in U.S. Pat. Nos. 4,513,006, 4,459,601 and 4,792,569. One of the compounds covered by U.S. Pat. No. 4,513,006, topiramate, has not only been found to exhibit particularly significant anticonvulsant activity in animals, but also appears to be useful in humans for the treatment of epilepsy (Drugs Future 1989, 14, 342).

While sulfamate compounds of the type disclosed in U.S. Pat. No. 4,513,006 have been shown to exhibit useful biological activity when administered to mammals, other compounds with equal or improved activity compared to topiramate would be desirable.

Presently, there are no previously reported sulfamate derivatives that contain the L-sorbopyranose structure. In addition, there are only two literature reports of L-sorbopyranose derivatives containing a 2,3-ketal or 2,3-acetal moiety (Chan, J. Y. C.; Cheong, P. O. L.; Hough, L.; Richardson, A. C. J. Chem. Soc. Perkin Trans. I, 1985, 1447 and Martin, O. R.; Korppi-Tommola, S. L.; Szarek, W. A. Can. J. Chem. 1982, 60, 1857).

Accordingly, it is an object of the present invention to describe novel sorbopyranose sulfamate derivatives with potent anticonvulsant activity.

SUMMARY OF THE INVENTION

It has been found that certain sulfamate derivatives represented by the formula (I):

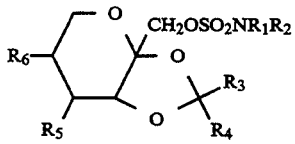

wherein $R_1$, $R_2$, $R_3$, $R_4$, $R_5$ and $R_6$ are as defined hereinafter exhibit anticonvulsant activity. As a result, the compounds and pharmaceutical compositions containing such compounds of the present invention are useful for the treatment of convulsions such as epileptic seizures. Compounds useful as intermediates to prepare compounds of the formula (I) are also included in this invention.

DETAILED DESCRIPTION OF THE INVENTION

More particularly, the present invention is directed to compounds represented by the following formula (I):

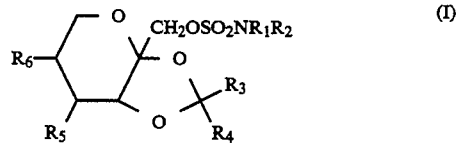

wherein $R_1$ and $R_2$ are the same or different and are selected from any of hydrogen or $C_1$ to $C_4$ alkyl. Preferably, $R_1$ and $R_2$ are each hydrogen.

$R_3$ and $R_4$ are the same or different and are selected from any of hydrogen or $C_1$ to $C_4$ alkyl. Preferably, $R_3$ and $R_4$ are each $C_1$ to $C_4$ alkyl.

$R_5$ and $R_6$ are the same or different and are selected from any of azido, halogen, hydroxyl, sulfamoyl ($H_2NSO_2O$), $C_1$ to $C_4$ alkoxy, $C_1$ to $C_4$ alkyl thiocarbonate (RSC(O)O), $C_1$ to $C_4$ alkyl carbonate (ROC(O)O), or $C_1$ to $C_4$ alkyl carboxylate (RC(O)O), wherein R is $C_1$ to $C_4$ alkyl. Preferably, $R_5$ and $R_6$ are selected from any of $C_1$–$C_4$ alkyl thiocarbonate, halogen or hydroxyl.

As used herein, the terms alkyl and alkoxy include straight and branched chains. For example, alkyl radicals include methyl, ethyl, propyl, isopropyl, n-butyl, isobutyl, and t-butyl. Halogen includes bromine, chlorine, fluoride and iodine.

Preferred compounds of the formula (I) are those wherein the pyran ring is in the L-sorbopyranose absolute configuration. Particularly preferred compounds of the formula (I) according to the present invention are those wherein the pyran ring is in the L-sorbopyranose absolute configuration, $R_1$ and $R_2$ are each hydrogen, $R_3$ and $R_4$ are each methyl; $R_5$ is methyl thiocarbonate ($CH_3SC(O)O$) and $R_6$ is halogen; or $R_5$ and $R_6$ are both halogen; or $R_5$ is hydroxyl and $R_6$ is halogen. Particularly preferred halogens include bromine, chlorine, and iodine. Examples of specific compounds of the formula (I) are:

5-deoxy-5-iodo-2,3-O-(1-methylethylidene)-4-[methylthiocarbonyl)]-α-L-sorbopyranose sulfamate, i.e. where the compound is in the L-sorbopyranose absolute configuration, $R_1$ and $R_2$ are hydrogen, $R_3$ and $R_4$ are methyl, $R_5$ is $CH_3SC(O)O$, and $R_6$ is iodine;

4,5-dibromo-4,5-dideoxy-2,3-O-(1-methylethylidene)-α-L-sorbopyranose sulfamate, i.e. where the compound is in the L-sorbopyranose absolute configuration, $R_1$ and $R_2$ are hydrogen, $R_3$ and $R_4$ are methyl, $R_5$ and $R_6$ are bromine;

and 5-chloro-5-deoxy-2,3-O-(1-methylethylidene)-α-L-sorbopyranose sulfamate, i.e. where the compound is in the L-sorbopyranose absolute configuration, $R_1$ and $R_2$ are hydrogen, $R_3$ and $R_4$ are methyl, $R_5$ is hydroxyl, and $R_6$ is chlorine.

Included within the scope of this invention are the various individual anomers, diastereomers and enantiomers as well as mixtures thereof. Such compounds are included within the definition of formula (I). In addition, the compounds of this invention include pharmaceutically acceptable salts, for example; alkali metal salts, such as sodium or potassium, ammonium salts, dialkyammonium salts, trialkylammonium salts, tetraalkylammonium salts, and tromethamine salts. Hydrates and other solvates of the compound of the formula (I) are also included within the scope of this invention.

The compounds of the formula (I) may be synthesized from compounds of the formulas (II–VI), wherein $R_1$, $R_2$, $R_3$, and $R_4$ are defined as previously described and X is equal to halogen, by one of the following methods. The various isomers, as shown, may be prepared by using the appropriate isomeric starting materials.

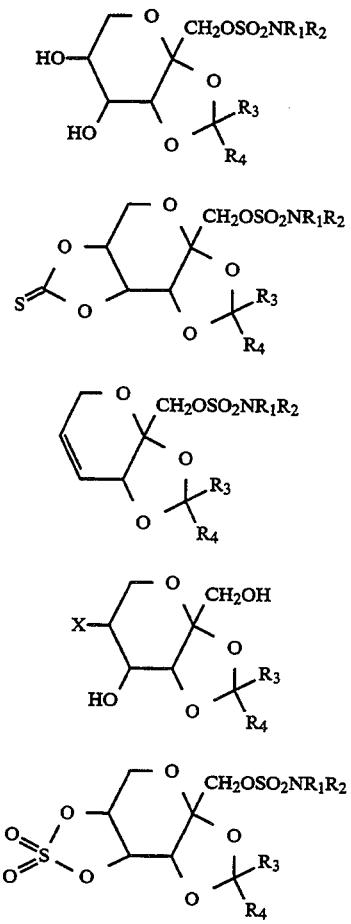

Alkyl carboxylates of the formula (I), where $R_5$ is RC(O)O and $R_6$ is halogen, may be prepared by reaction of a diol of the formula (11) with an acid halide, such as acetyl bromide, in refluxing acetonitrile according to the procedure of Mansuri et al. described in J. Org. Chem. 1989, 54, 4780. For example:

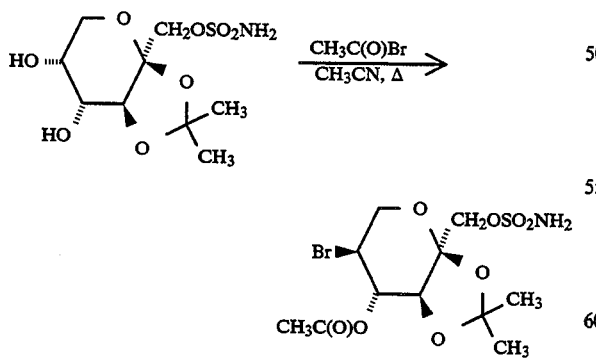

Halothiocarbonates of the formula (I), where $R_5$ is RSC(O)O and $R_6$ is halogen, may be prepared by reaction of a diol of the formula (II) with 1,1'-thiocarbonyldiimidazole in the presence of a suitable aprotic solvent, such as tetrahydrofuran, dichloromethane, or ethyl acetate, to furnish the corresponding thiocarbonates of the formula (III), which is subsequently reacted with an alkyl halide, such as methyl iodide, in the presence of a suitable ethereal solvent, such as 1,2-dimethoxyethane or tetrahydrofuran, at temperatures above 60° C. in a sealed vessel, to provide the halothiocarbonate of the formula (I). For example:

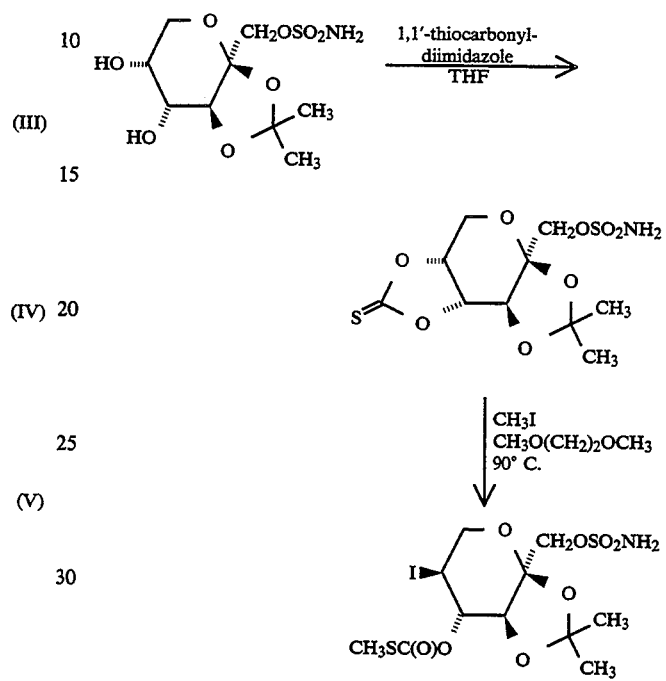

Dihalo compounds of the formula (I), where $R_5$ and $R_6$ are both halogen, may be prepared by the low temperature addition of halogen halides, such as bromine, iodine, iodine monobromide, and iodine monochloride, to alkenes of the formula (IV) in dichloromethane, chloroform, or toluene at temperatures of from about −78° C. to 0° C. The requisite alkenes of the formula (IV) may be prepared via reduction of halothiocarbonates of the formula (I) with trialkyl phosphites according to the procedure of Corey and Winter described in J. Am. Chem. Soc. 1963, 85, 2677 or preferably by reduction with Mg(Hg) or zinc as described by Vedejs and Wu in J. Org. Chem. 1974, 39, 3641. For example:

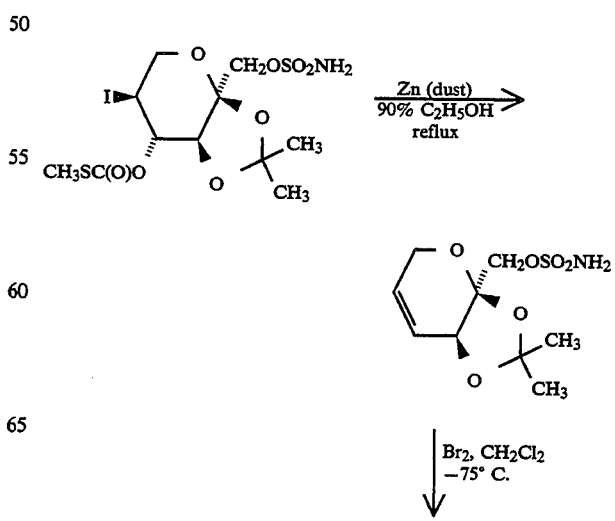

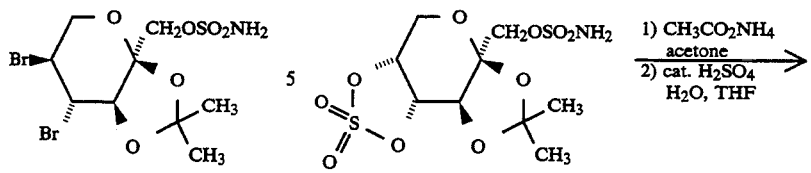

Halohydrin compounds of the formula (I), where $R_5$ is hydroxyl and $R_6$ is halogen, may be prepared by the reaction of sulfamoyl chloride ($ClSO_2NH_2$) with a halohydrin compound of the formula (V) in a polar aprotic solvent, such as tetrahydrofuran or N,N-dimethylformamide, at temperatures of from about $-60°$ C. to $30°$ C. For example:

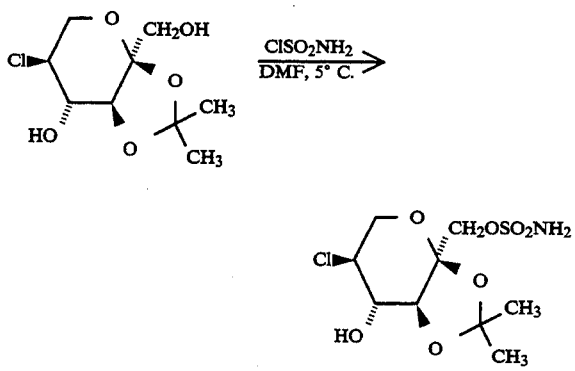

Similarly, compounds of the formula (I) where $R_5$ is sulfamoyl or $C_1$ to $C_4$ alkyl carbonate and $R_6$ is halogen may be prepared by the reaction of halohydrins of the formula (I) with sulfamoyl chloride or alkyl chloroformate, respectively, in a solvent such as tetrahydrofuran or N,N-dimethylformamide, at temperatures of from about $-60°$ C. to $30°$ C. For example:

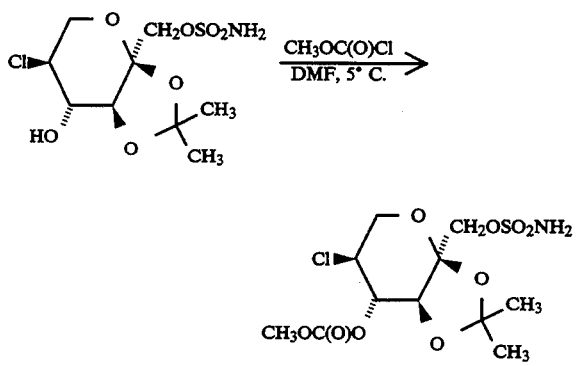

Compounds of the formula (I) where $R_5$ is hydroxyl and $R_6$ is either halogen, $C_1$ to $C_4$ alkoxy, or $C_1$ to $C_4$ alkyl carboxylates may be prepared by the reaction of a cyclic sulfate of the formula (VI) with halide salts, $C_1$ to $C_4$ alkoxide salts, or $C_1$ to $C_4$ carboxylic acid salts, respectively, followed by acid hydrolysis according to the procedures described by Sharpless et al. in J. Am. Chem. Soc. 1988, 110, 7538 and Tetrahedron Lett. 1989 30, 655. For example:

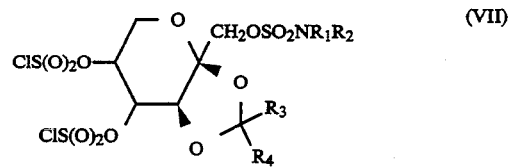

The starting materials required to synthesize compounds of formula (I) may be prepared by methods known to those skilled in the art of organic synthesis. For example, diols of the formula (II) can be prepared by the procedure described by Maryanoff et al. in J. Med. Chem. 1987, 30, 880. Halohydrin compounds of the formula (V) may be prepared by the method of Martin et al. in Can. J. Chem. 1982, 60, 1857. Cyclic sulfates of the formula (VI) may be prepared, for example, by reacting a diol of the formula (II) with sulfuryl chloride in the presence of pyridine or triethylamine at a temperature of about $-78°$ to about $25°$ C. in an aprotic solvent such as ethyl acetate, toluene, or dichloromethane to produce the bis-chlorosulfate of formula (VII).

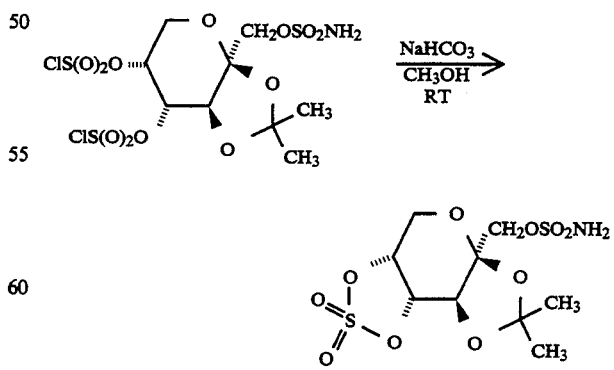

Dechlorosulfation of the bis-chlorosulfate of formula (VII) with a weak base, such as $NaHCO_3$ or pyridine, in an alcohol such as methanol or ethanol at temperatures from $-40°$ to $25°$ C. yields cyclic sulfate compounds of the formula (VI). For example:

Pharmaceutically acceptable salts of the compounds of formula (I) may be prepared by reacting the sulfamate of formula (I) with the appropriate base and recovering the salt. For example:

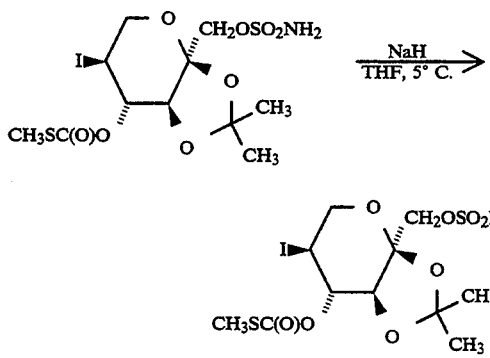

Compounds of the formulas (III), (IV), and (V), with the proviso that $R_3$ and $R_4$ can not both be methyl at the same time for compounds of formula (V), are useful as intermediates to prepare compounds of the formula (I) and are included in this invention.

The compounds of formula (I) are particularly useful as anticonvulsant agents in mammals including humans. The anticonvulsant activity of the subject compounds was determined using a standard "maximal electroshock test" (MES). In this test, activity is indicated by a block of the toxic extensor seizure caused by application of an electric shock to mice via corneal electrodes, as described by Swinyard et al. in J. Pharmacol. Expt. Ther. 1952, 106, 319, and recorded as % block. A more recent description of current anticonvulsant drug screening is given by Swinyard in Epilepsia 1978, 19, 409.

In the test, albino male CRS-CD1 mice weighing between 18-25 g were used in all experiments (obtained from Charles River). They were allowed food and water ad libitum and were used only once. The electroshock apparatus and the corneal electrodes were purchased from Wahlquist Instrument Company, Salt Lake City, Utah.

Maximal electroshock seizures were induced by the delivery of a 60 Hertz (Hz) current of 50 milliamps (mA) intensity to the mouse through corneal electrodes for 0.2 seconds as originally described by Swinyard (1952). This stimulus intensity is approximately 4 to 6 times the current producing 100% tonic extensor convulsions. During the validation of the MES test, the duration of the various seizure components following maximal electroshock were measured as follows: hindleg tonic flexion was measured from the time of the application of the stimulus to the time of onset of hindleg tonic extension (i.e. when the hindlegs deviate by greater than an angle of 90° from the torso), hindleg tonic extensor was measured from the time of extensor thrust to the onset of generalized clonus, and terminal clonus was measured from the beginning to the end of bilateral rhythmic clonic jerking. Mortality was also recorded. The duration of each seizure component agreed well with the values previously reported by Tedeschi et al. in J. Pharmacol. Expt. Ther. 1955, 116, 107. The corneal electrodes were concave so that saline could be applied to the electrodes to reduce mortality. If this procedure is followed, mortality should always be less than 40% in control mice. Thus, at an electroshock stimulus of 60 Hz, 50 mA and 0.2 seconds duration, the order of convulsive components and the percentage of control animals displaying the behaviors should be as follows: tonic flexion (100%), tonic extension (100%) and clonus (100%) with less than 40% mortality.

For testing compounds, the abolition of the tonic extensor component was the endpoint. Animals were dosed orally (PO) with either vehicle or test drug and at a specified time were given a maximal electric shock through corneal electrodes blotted with saline (as described above). A minimum of 10 animals were used per group and the percentage of animals in the group without tonic hindlimb extension recorded. The anticonvulsant activity of the compounds of this invention tested according to the Swinyard (1952) method is shown in the following Table I.

TABLE I
ANTICONVULSANT ACTIVITY DATA

| Compound of Example | $R_5$ | $R_6$ | Dose (mg/kg, p.o) | MES test (mouse) % Block at 4 hours |
|---|---|---|---|---|
| 1 | MeSC(O)O | I | 75 | 90 |
| 2 | Br | Br | 75 | 100 |
| 3 | OH | Cl | 75 | 100 |

For treating epilepsy, a compound of formula (I) may be employed at a daily dosage in the range of about 10 to 2000 rag, usually in 1 to 4 daily divided doses, for an average adult human. A unit dose would contain about 5 to 500 mg of the active ingredient. This translates to a dose of about 0.1 to 30 mg/kg/day.

In general, compounds of formula (I) may be used in treating epilepsy in a manner similar to that used for phenytoin; e.g., orally administering a solid formulation twice/day. Medical aspects of the treatment of epilepsy are described in greater detail by L. S. Goodman et al. in "The Pharmacological Basis of Therapeutics", 5th Ed. pages 201 to 226, Macmillan (1975).

The compounds of formula (I) preferably are administered in the form of a pharmaceutical composition. To prepare the pharmaceutical compositions of this invention, one or more sulfamate compounds of formula (I) are intimately admixed with a pharmaceutical carrier according to conventional pharmaceutical compounding techniques, which carrier may take a wide variety of forms depending on the form of preparation desired for administration, e.g., oral, by suppository, or parenteral. In preparing the compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. Suppositories may be prepared, in which case cocoa butter could be used as the carrier. For parenterals, the carrier will usually comprise sterile water, though other ingredients, for purposes such as aiding solubility or for preservation, may be included. Injectable suspensions may also be prepared, in which case appropriate liquid carriers, suspending agents, and the like may be employed.

It is especially advantageous to formulate the aforementioned pharmaceutical compositions in unit dosage form for ease of administration and uniformity of dosage. The term "unit dosage form" as used in the specification and Claims herein refers to physically discrete units suitable as unit dosages, each unit containing a predetermined quantity of active ingredient calculated to produce the desired therapeutic effect in association with the required pharmaceutical carrier.

The pharmaceutical compositions herein will contain, per unit dosage, e.g., tablet, capsule, powder, injection, teaspoonful, suppository and the like. The compositions will be administrated in amounts as previously described herein with regard to the active ingredient and to the condition being treated. The dosages, however, may be varied depending upon the requirement of the patient, the severity of the condition being treated, and the compound being employed. Determination of optimum dosages for a particular situation is within the skill of the art.

In the following Examples and throughout the specification the following terms and abbreviations are used: g (grams); mL (milliliters); min (minutes); hr (hours); mol (moles); N (normal); v/v (volume to volume); DMF (N,N-dimethylformamide); EtOAc (ethyl acetate); THF (tetrahydrofuran); RT (room temperature); C, H, N, etc. (the chemical symbols for the elements); Calcd. (calculated); $[\alpha]_D^{25}$ (specific rotation measured at 25° C. with 589 nanometer light ); c (concentration in grams per 100 mL) $^1$H NMR (proton nuclear magnetic resonance spectrum); MS (mass spectrum); mp (melting point); and Celite ® (filter agent). All melting points are corrected.

EXAMPLE 1

5-Deoxy-5-iodo-2,3-O-(1-methylethylidene)-4-[methylthiocarbonyl)]-α-L-sorbopyranose Sulfamate.

2,3-O-(1-Methylethylidene)-β-D-fructopyranose 1-sulfamate (32.5 g, 0.109 mol; J. Med. Chem. 1987, 30, 880) was combined with 1,1'-thiocarbonyldiimidazole (47.3 g, 0.239 mol), dissolved in 500 mL of THF, and stirred at RT for 6 hr. The solvent was removed in vacuo at 40° C. and the residue was dissolved in EtOAc. The EtOAc solution was extracted sequentially twice with 1 N HCl, three times with saturated aqueous NaHCO$_3$, once with saturated aqueous NaCl, dried over anhydrous MgSO$_4$, filtered through Celite ®, and concentrated in vacuo at 40° C. to furnish 36.7 g of crude product as brown oil. This material was purified by chromatography on silica gel eluting with CH$_2$Cl$_2$/EtOAc (4:1 v/v) to provide 15.0 g (40%) of 2,3-O-(1-methylethylidene)-4,5-O-thiocarbonyl-β-D-fructopyranose sulfamate as a white solid. An analytical sample was recrystallized from anhydrous ethanol, m.p. 205°-206° C.; $[\alpha]_D^{20}= -75.1°$ (c=1.75, CH$_3$OH).

Anal. Calcd. for C$_{10}$H$_{15}$NO$_8$S$_2$:C, 35.19; H, 4.43; N, 4.10, S, 18.78. Found: C, 35.40; H, 4.46; N, 4.06, S, 18.84.

2,3-O-(1-Methylethylidene)-4,5-O-thiocarbonyl-β-D-fructopyranose sulfamate (11.11 g, 0.033 mol), methyl iodide (40 6 mL, 0.652 mol) and 1,2-dimethoxyethane (100 mL) were combined in a pressure bottle and heated at 90° C. while stirring for 10 hr. The solvent was removed in vacuo and the residue was purified via chromatography on silica gel eluting with CH$_2$Cl$_2$/EtOAc (6:1 v/v) to give a white solid (10.43 g, 65%) which was recrystallized from CH$_2$Cl$_2$/EtOAc to provide the title compound as a white crystalline solid; m.p. 135°-136° C.; $[\alpha]_D^{25}= +39.4°$ (c=1.00, CH$_3$OH).

Anal. Calcd. for C$_{11}$H$_{18}$INO$_8$S$_2$: C, 27.34; H, 3.75; N, 2.90, S, 13.27. Found: C, 27.49; H, 3.52; N, 2.84, S, 13.90.

EXAMPLE 2

4,5-Dibromo-4,5-dideoxy-2,3-O-(1-methylethylidene)-α-L-sorbopyranose Sulfamate.

5-Deoxy-5-iodo-2,3-O-(1-methylethylidene)-4-[methylthiocarbonyl)]-α-L-sorbopyranose sulfamate (Example 1; 14.09 g, 0.029 mol), zinc dust (11.45 g, 0.175 mol), H$_2$O (14 mL) and 95% ethanol (140 mL) were combined and heated at reflux while vigorously stirring for 2 hr. After cooling to RT, the reaction was filtered through Celite ® and concentrated in vacuo to give 15.5 g of a brown oil, which was purified via chromatography on silica gel eluting with CH$_2$Cl$_2$/EtOAc (9:1 v/v) to provide 5.42 g of product. This material was dissolved in CHCl$_3$ and extracted twice with saturated aqueous NaCl, dried over anhydrous MgSO$_4$, filtered through Celite ® and concentrated in vacuo to give 5.43 g of 4,5-dideoxy-2,3-O-(1-methylethylidene)-β-D-fruct-4-enopyranose sulfamate solvate with chloroform (8:1) as a golden oil; $[\alpha]_D^{25} -0.9°$ (c=1.13, CH$_3$OH).

Anal. Calcd. for C$_9$H$_{15}$NO$_6$S.⅛ CHCl$_3$: C, 39.11; H, 5.44; N, 5.00. Found: C, 39.25; H, 5.31;N, 4.86.

A solution of 4,5-dideoxy-2,3-O-(1-methylethylidene)-β-D-fruct-4-enopyranose sulfamate (1.04 g, 0.0039 mol) in 12 mL of dry CH$_2$Cl$_2$ was cooled to −75° C. while stirring under an argon atmosphere. Bromine (0.51 mL, 0.0098 mol) was added dropwise over 10 min and the reaction was stirred at −75° C. for 1 hr, quenched by the addition of cyclohexene (1 mL, 0.0098 mol), basified with pyridine (0.8 mL, 0.0098 mol), warmed to RT, and purified by chromatography on silica gel eluting with CH$_2$Cl$_2$/EtOAc (19:1 v/v) to give 1.10 g (66%) of the title compound as a clear glass; $[\alpha]_D^{25}= +20.1°$ (c=1.00, CH$_3$OH).

Anal. Calcd. for C$_9$H$_{15}$Br$_2$NO$_6$S: C, 25.43; H, 3.56; Br, 37.59; N, 3.29; S, 7.54. Found: C, 25.71; H, 3.61; Br, 37.49; N, 3.24; S, 7.61.

EXAMPLE 3

5-Chloro-5-deoxy-2,3-O-(1-methylethylidene)-α-L-sorbopyranose Sulfamate.

A solution of 5-chloro-5-deoxy-2,3-O-(1-methylethylidene)-α-L-sorbopyranose (3.00 g, 0.013 mol; Can. J. Chem. 1982, 60, 1857)in dry DMF (25 mL) was cooled to 5° C. while stirring under an argon atmosphere. Sulfamoyl chloride (2.33 g, 0.020 mol) was added and the reaction was stirred at 5° C. for 2.5 hr, diluted with 100 mL of saturated aqueous NaCl, and extracted with three portions of EtOAc. The combined EtOAc extracts were extracted twice with saturated aqueous NaHCO$_3$, dried over anhydrous MgSO$_4$, filtered through Celite ®, and concentrated in vacuo at 40° C. The residue was purified by chromatography on silica gel eluting with CH$_2$Cl$_2$/EtOAc (4:1 v/v) and subsequently recrystallized from CH$_2$Cl$_2$/hexane (2:3) to yield 1.38 g (35%) of the title compound as a white crystalline solid that also contained 0.14 equivalents of 5-chloro-5-deoxy-2,3-O-(1-methylethylidene)-4-sulfamoyl-α-L-sorbopyranose sulfamate (as determined by MS, $^1$H NMR, and elemental analysis); mp 94°–100° C.; $[\alpha]_D^{25} = +7.7°$ (c=1.00, CH$_3$OH).

Anal. Calcd. for $C_9H_{16}ClNO_7S.0.14$ $C_9H_{17}ClN_2O_9S_2$: C, 33.01; H, 4.96; N, 4.80; S, 10.99. Found: C, 33.15; H, 5.01; N, 4.88; S, 10.94.

What is claimed is:

1. A compound represented by the formula (I):

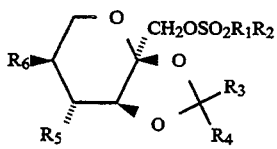

wherein $R_1$ and $R_2$ are the same or different and selected from any of hydrogen or $C_1$ to $C_4$ alkyl;
wherein $R_3$ and $R_4$ are the same or different and are selected from any of hydrogen or $C_1$ to $C_4$ alkyl;
wherein $R_5$ and $R_6$ are the same or different and are selected from any of azido, halogen, hydroxyl, sulfamoyl ($H_2NSO_2O$), $C_1$ to $C_4$ alkoxy, $C_1$ to $C_4$ alkyl thiocarbonate (RSC(O)O), $C_1$ to $C_4$ alkyl carbonate (ROC(O)O), or $C_1$ to $C_4$ alkyl carboxylate (RC(O)O), wherein R is $C_1$–$C_4$ alkyl; the enantiomers and mixtures thereof; and the pharmaceutically acceptable salts and solvates thereof.

2. The compound of claim 1, wherein $R_1$ and $R_2$ are each hydrogen.

3. The compound of claim 1, wherein $R_3$ and $R_4$ are each methyl.

4. The compound of claim 1, wherein $R_1$ and $R_2$ are each hydrogen, $R_3$ and $R_4$ are each methyl, $R_5$ is methyl thiocarbonate (CH$_3$SC(O)O) and $R_6$ is iodine.

5. The compound of claim 1, wherein $R_1$ and $R_2$ are each hydrogen, $R_3$ and $R_4$ are each methyl, and $R_5$ and $R_6$ are each bromine.

6. The compound of claim 1, wherein $R_1$ and $R_2$ are each hydrogen, $R_3$ and $R_4$ are each methyl, $R_5$ is hydroxyl, and $R_6$ is chlorine.

7. A pharmaceutical composition comprising a therapeutically effective amount of the compound of claim 1 and a pharmaceutically acceptable carrier.

8. The pharmaceutical composition of claim 7, wherein the therapeutically effective amount is an effective amount for treating convulsions.

9. A method of treating a mammal suffering from convulsions comprising treating that mammal with the compound of claim 1 in an amount sufficient to treat the convulsions.

* * * * *